United States Patent [19]

Hanson et al.

[11] Patent Number: 4,900,847
[45] Date of Patent: Feb. 13, 1990

[54] CATALYTIC ASYMMETRIC EPOXIDATION

[75] Inventors: Robert M. Hanson; Soo Y Ko, both of Cambridge; Karl B. Sharpless, Brookline, all of Mass.

[73] Assignee: Massachusetts Institute of Technology, Cambridge, Mass.

[21] Appl. No.: 833,572

[22] Filed: Feb. 24, 1986

Related U.S. Application Data

[63] Continuation of Ser. No. 719,776, Apr. 4, 1985, abandoned.

[51] Int. Cl.$^4$ ............................................. C07D 301/19
[52] U.S. Cl. ...................................................... 549/529
[58] Field of Search ......................................... 549/529

[56] References Cited

U.S. PATENT DOCUMENTS 4,021,454  5/1977  Wulff et al. ........................... 549/529
4,471,130  9/1984  Katsuki et al. ....................... 549/529

FOREIGN PATENT DOCUMENTS 2029212  10/1970  France ................................. 549/529

OTHER PUBLICATIONS

J. Gordon Hill et al., J. Org. Chem. (1983), vol. 48, pp. 3607–3608.
H. Langhals et al., Chemische Berichte, vol. 113 (1980), pp. 3662–3665.
K. Barry Sharpless, Chemistry in Britain, Jan. 1986, pp. 38–44.
R. A. Sheldon, Journal of Molecular Catalysis, vol. 7 (1980), pp. 107, 114–117.
R. A. Sheldon et al., Metal-Catalyzed Oxidations of Organic Compounds, Academic Press, (1981), pp. 56–62, 284–285.
Mark B. Ward et al., Journal of Molecular Catalysis, vol. 27 (1984), pp. 1–10.
K. Barry Sharpless et al., Aldrichimica Acta, vol. 12(4) (1979) pp. 63–74.

Primary Examiner—Glennon H. Hollrah
Assistant Examiner—Amelia A. Owens
Attorney, Agent, or Firm—Bertram I. Rowland

[57] ABSTRACT

Improved method for epoxidation of ethylenic alcohols is provided employing catalytic amounts of a titanium-glycol catalyst and a peroxide under mild conditions which provide for the continuous maintenance of an anhydrous medium during catalyst formation and during the course of the reaction. Conveniently, molecular sieves may be employed.

9 Claims, No Drawings

CATALYTIC ASYMMETRIC EPOXIDATION

CROSS-REFERENCE TO RELATED APPLICATION

This application is a Continuation of application Ser. No. 719,776, filed Apr. 4, 1985 now abandoned, which disclosure is incorporated herein by reference.

BACKGROUND OF THE INVENTION

1. Field of the Invention

The synthetic production of a wide variety of drugs and naturally occurring products is dependent upon the introduction of an oxygen functionality at a particular site. Frequently, the oxygen functionality may be associated with a second functionality in the vicinal position. For many compounds of interest, one or both of these sites may be chiral. The epoxide functionality is a particularly attractive functionality for providing the two substituents. Furthermore, where the epoxide can be provided as a particular enantiomer or diastereomer, by appropriate selection of reagents and conditions, one can provide for the correct stereoisomers at the two positions. There is, therefore, substantial interest in ways to prepare epoxides in high yield providing for asymmetric formation of the epoxide.

2. Description of the Prior Art

U.S. Pat. No. 4,471,130 describes asymmetric epoxidation of ethylenic alcohols employing, for the most part, stoichiometric amounts of metal alkoxide catalyst. Numerous other articles have been published employing the process described in the above-cited U.S. patent, using a wide variety of olefinic alcohols for epoxide formation, substantially following the stoichiometric conditions described in the cited patent. The disclosure of U.S. Pat. No. 4,471,130 is incorporated herein by reference in its entirety.

SUMMARY OF THE INVENTION

Olefinic alcohols are asymmetrically epoxidized employing an organic hydroperoxide, a glycol chelated titanium catalyst, where the glycol is optically active, and the olefinic alcohol, in an inert organic solvent, under conditions where the catalyst and reaction mixture are maintained substantially anhydrous by a dehydrating environment and hydrolysis of the epoxide and/or catalyst is inhibited.

DESCRIPTION OF THE SPECIFIC EMBODIMENTS

Methods and compositions are provided for preparing epoxides of olefinic alcohols asymmetrically, where the olefin is from 0 to 1 carbon atoms from the carbinol carbon atom. The olefinic alcohol can vary widely, being at least three carbon atoms and not more than about 60 carbon atoms, more usually not more than about 36 carbon atoms. However, polymers of allylic or homoallylic alcohols may be employed where some or a plurality of the olefinic groups may be epoxidized in accordance with the subject invention. The olefinic alcohol may be aliphatic, alicyclic, aralkyl or heterocyclic substituted alkyl or heterocyclic, where the heteroatoms do not interfere with the reaction, such as oxy ether, sulfone, polysubstituted amino, usually 3 to 4 substituents, or the like.

The allylic groups may be mono-, di-, tri- or tetra-substituted ethylenes with aliphatic, alicyclic or aromatic groups, particularly aliphatic and alicyclic groups, and the olefin may be exocyclic or endocyclic.

For the most part, the substrates will have the following partial formula:

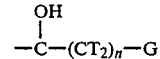

wherein:
where one of the atoms bonded to the carbinol carbon will usually be hydrogen;
n is 0 to 1;
T can be any inert group, free of active functionalities such as basic amines and acidic groups; and
G is an olefinic group and may be 60 carbon atoms or more, more usually not more than about 30 carbon atoms and is bonded through an olefinic carbon atom.

In view of the enormous diversity of carbinols which may be employed as substrates, only various classes of products of interest can be suggested as useful in the subject process, either for synthesis of a particular product, for preparing an intermediate, or for modification of an existing product, particularly a natural product.

The subject invention can be used in organic synthesis of enantiomers, both for introduction of a variety of functionalities in a synthetic procedure and optical resolution of an enantiomer from a racemic mixture. The sole requirements for use of the subject invention and syntheses and/or resolution are the presence of (1) an hydroxyl group; (2) a chiral or prochiral center, which may or may not involve the carbinol carbon; and (3) an olefin.

General classes of compounds of interest include steroids, lipids, prostaglandins, terpenoids, hormones, saccharides, CNS drugs, α- and β-adrenergic blocking agents, antiarrythmic drugs, vasodilator drugs, analgesics, antibiotics, and the like. Of particular interest are those compounds which have a three carbon unit, where the three carbon unit includes at least two oxy functionalities, at least one of which has a chiral carbon, and the third carbon may lack a heterofunctionality, or have a heterofunctionality, such as amino, thio, or the like.

The catalyst which is employed is extensively described in U.S. Pat. No. 4,471,130. For the subject invention, the catalyst will employ quadrivalent titanium ($Ti^{+4}$) chelated with an asymmetric glycol, where the glycol may be substituted with heteroatom containing functionalities or unsubstituted with heteroatom containing functionalities. The glycol will be at least 4 carbon atoms and may be up to about 36 carbon atoms, usually not more than about 30 carbon atoms, and preferably not more than about 20 carbon atoms.

Of particular interest as the glycol are derivatives of tartaric acid, both esters and amides, where the esters may have alkoxy groups of from 1 to 12, usually 1 to 6, more usually 1 to 3 carbon atoms, preferably methyl, ethyl and isopropyl, and the amides may have unsubstituted, mono- or disubstituted amino groups, where the substituents on the nitrogen may be from about 1 to 12 carbon atoms, usually from 1 to 6 carbon atoms, more usually from about 1 to 3 carbon atoms.

The glycol should be free of groups which interfere with the reaction, groups which react with the peroxide under the conditions of the epoxidation, groups which might displace the asymmetric glycol from the titanium, or the like.

In addition to the glycol, alkoxides are employed having a single oxy functionality linked to titanium, where the alkoxide will normally be non-chiral and free of functionalities which might interfere with the reaction. For the most part, the alkoxides will be aliphatic alcohols of from 1 to 12, generally of from 1 to 6, and preferably of from 3 to 6 carbon atoms. Preferably, the alkoxides will be relatively bulky, being branched at the α carbon atom, normally having from 1 to 2 branches. Particularly preferred is isopropoxide and tert.-butoxide. It should be clearly understood that the alkanols are primarily chosen for convenience and any alkanol may be employed, so long as the substituents on the alkanol do not interfere with the course of the reaction.

The preparation of the catalyst is conventional and can be performed in situ. For example, an alkoxide substituted dihalo metal may be combined with the chiral glycol, as a metal dialkoxide, e.g., lithium or sodium, in an inert polar solvent and the product separated from the inorganic salt. More conveniently, the titanium tetraalkoxide may be combined with the chiral glycol in approximately stoichiometric amounts in an inert solvent. There is no requirement that the alcohol which is formed be removed, although it may be removed, for example, by distillation.

The hydroperoxides which are employed for the epoxidation may be aliphatic, alicyclic, or aralkyl hydroperoxides, preferably being tertiary hydroperoxides, more preferably having at least two aliphatic carbon atoms bonded to the carbon bonded to the hydroperoxide group. The hydroperoxide will generally be from about 3 to 20 carbon atoms, more usually from about 3 to 12 carbon atoms, particularly hydroperoxides having acceptable thermostability.

Illustrative hydroperoxides include t.-butylhydroperoxide, α,α-dimethylheptyl hydroperoxide, bis-diisobutyl-2,5-dihydroperoxide, 1-methylcyclohexyl hydroperoxide, cumene hydroperoxide, cyclohexyl hydroperoxide, and trityl hydroperoxide.

As the reaction medium, inert solvents will be employed, particularly halohydrocarbon solvents of from 1 to 3 carbon atoms, preferably from 1 to 2 carbon atoms. A solvent which has been found to be quite satisfactory is methylene dichloride. All of the materials employed should be substantially free of water prior to being added to the reaction mixture. In addition, water formation and accumulation should be inhibited by the rapid removal of any water which may form in the reaction mixture. The removal of water can be achieved in a variety of ways.

Water can be directly removed by adding to the reaction mixture various reagents which will strongly bind water, so as to substantially remove its activity as a hydrolyzing agent, while not interfering in the course of the reaction. Conveniently, zeolites may be employed as a powder or small particles which may be introduced in the mixture in sufficient amount to absorb any of the water which is formed. Zeolites of interest include zeolite 3A, zeolite 4A, and zeolite 5A. Other dehydrating agents may also find use, such as silica gel, alumina, orthoesters, e.g., carbonates, amide acetals, e.g., dimethyl formamide dimethyl acetal, and the like. Any material which can serve to bind the water, so as to substantially inhibit its reactivity, while not interfering with the course of the reaction may be employed in the reaction mixture. Alternatively, a device such as a Soxhlet extractor may be employed, where the water containing solvent is continuously vaporized, condensed and passed through a dehydrating medium.

Mild conditions will normally be employed, with temperatures below about 80° C., usually below about 30° C., and generally in the range of about −100° to 20° C., more usually in the range of about −50° to 10° C. The reaction is desirably carried out under an inert atmosphere, conveniently nitrogen.

In carrying out the epoxidation, the dehydrating agent will be added prior to the occurrence of any significant amount of reaction. For best results the dehydrating agent is introduced prior to or at the beginning of the catalyst preparation. It is found that rates of epoxidation are enhanced by preparation of the catalyst in the presence of the dehydrating agent. The amount of dehydrating agent to be employed will vary with the choice and manner of dehydration and may be determined empirically. The amount of dehydrating agent employed may vary from 5 to 1000, usually from about 100 to 500 weight percent based on catalyst. All of the dehydrating agent may be added initially or portions may be added from time to time.

The titanium catalyst can be pre-prepared or conveniently prepared in situ. In preparing the catalyst, the titanium alkoxide is combined with the chiral glycol in a dry inert solvent, preferably in the presence of a dehydrating agent, at a temperature below about 30° C. and in about stoichiometric proportions, although small excesses, generally less than about 100, usually less than about 50 mole percent excess, of the chiral glycol may be employed. The reaction is then allowed to proceed for a sufficient time for the catalyst to form. Particularly, titanium tetraisopropoxide may be combined with tartrate diester, diamide or half-ester amide.

Usually, the reaction forming the catalyst is complete in less than about 30 min, more usually in less than about 15 min. The time is not critical and can be optimized for a particular set of conditions and materials. The amount of catalyst employed will generally be less than about 25 mole percent based on olefinic alcohol, more usually less than about 20 percent and usually in excess of about 1 percent, generally from about 3 to 12 mole percent, more usually from about 5 to 10 mole percent.

The hydroperoxide is normally added in at least stoichiometric amount based on total olefinic alcohol, and preferably in excess, usually at least 25 percent excess, more usually at least 50 percent excess and not more than about 500 percent excess, that is, about 1 to 5 equivalents, preferably from about 1 to 2 equivalents of the hydroperoxide will be used per olefin equivalent. Of particular interest is the use of either tert.-butyl hydroperoxide or aralkyl t.-hydroperoxide, e.g., cumene hydroperoxide, the latter finding particular use with low molecular weight olefinic alcohols.

The concentrations of the various materials may be varied widely, the olefinic alcohol normally being from about 0.005 to about 2M, preferably being from about 0.05 to 1M. The concentrations of the other reactants will be related accordingly.

The hydroperoxide reacts with the catalyst in a reaction which is usually complete in less than about 1 hr, usually less than about 30 min. The order of addition is not critical, so that the hydroperoxide and olefinic carbinol can be added consecutively in any order or concurrently. Where the hydroperoxide is added initially, the olefinic carbinol may be added after completion of the reaction between the catalyst and hydroperoxide.

After all the reactants have been combined in the inert medium in the presence of the dehydrating agent, the reaction is continued until the substrate has been transformed to the desired degree. The rate of the reaction varies depending upon the conditions and the amount of material involved and may vary from a few minutes to a few days. By employing continuous dehydration premature deactivation of the catalyst is prevented, rates are accelerated, so that shorter times are required than when carrying out the reaction in the absence of continual dehydration, even in the presence of higher amounts of catalyst. Reactions are frequently complete within about 2 to 3 hr at −20° C.

After completion of the reaction, the reaction may be worked up in a variety of conventional ways. The catalyst may be destroyed using a mildly acidic or basic aqueous solution and where the epoxidized olefin is in the organic layer, the organic layer is isolated, dried, and the product isolated. For water soluble products, salting out, extraction, chromatography or distillation may be required. Purification of the product may then be carried out in accordance with conventional means.

If desired, the epoxide may be further reacted to form the monoester. By employing an acylating agent, e.g., carboxylating, sulfonylating, etc., which has been or is activated, e.g., acyl halide or anhydride in the presence of a tertiary amine, at temperatures in the range of about −50° to 20° C., the monoester epoxide may be obtained. The product may then be isolated by conventional work up.

Alternatively, the epoxide ring may be opened by employing a combination of a nucleophile and at least a stoichiometric amount of a metal ester, e.g., titanate, zirconate, etc., particularly aliphatic esters, more particularly alkyl esters. The metal esters provide for improved regioselectivity. The reaction is carried out under mild conditions, generally from about −20° to 80° C., usually from about 0° to 40° C. The nucleophile will usually be in greater than stoichiometric amount, usually at least 1-fold excess. Nucleophiles include halide ions, amines, azide, mercaptans, mercaptides, selenides, cyanide, carboxylates, alkoxides, phenoxides, or the like. Various organic solvents may be employed, both polar and non-polar. Enhanced regioselectivity is achieved, with opening preferably occurring at the 3-carbon atom from the hydroxyl of the glycidyl alcohol. Prior to the epoxide opening, any hydroperoxide present may be destroyed, using various conventional reagents.

The following examples are offered by way of illustration and not by way of limitation.

EXPERIMENTAL

Example 1

Exemplary Reactions, Reagents and Equipment (1) All glass equipment was flame-dried under vacuum just prior to use, however this was found generally not to be necessary.

(2) Molecular sieves used in the reaction were of commercial grade, purchased as the activated (4A) or unactivated (3A) 2-3μ powder (Aldrich). Molecular sieves used for storage or drying of solvents were in the pellet form (Linde). Activation of the unactive molecular sieves was accomplished by heating at 250°-300° for several hours under 0.05 mm pressure.

(3) The dichloromethane used as reaction solvent was generally freshly distilled from calcium hydride prior to use, however this was observed to be necessary only for small scale (<10 mmol) reactions.

(4) Dialkyl tartrate was distilled, stored under argon or nitrogen, and dispensed by gastight syringe.

(5) Titanium (IV) isopropoxide was of commercial grade and dispensed by gastight syringe.

(6) Tert.-butyl hydroperoxide (TBHP) was used as a 50% solution in dichloromethane, prepared from 70% aqueous TBHP by dilution with dichloromethane, phase separation, azeotropic removal of water, and sequential drying over molecular sieves. The solution was stored at −20° over 3 A or 4 A molecular sieve pellets. Just prior to use, somewhat more than the required amount of this solution was allowed to stand over a small amount of activated 3 A or 4 A molecular sieve pellets at room temperature for several minutes.

(7) All allylic alcohols were synthesized, except for geraniol, which was of commercial grade, and cinnamyl alcohol, which was distilled at 0.2 mm. All alcohols were dissolved in dichloromethane (about three volumes) and dried as described above for TBHP just prior to use.

(8) Reactions were monitored by either thin layer chromatography (silica, petroleum ether/ethyl acetate:4/1 or petroleum ether/ethyl ether:1/1; anisaldehyde/sulphuric acid/ethanol developer) or capillary GPLC (SE-30, helium, 60°-120°).

(9) The reactions were quenched in one of five ways:

(a) For analysis of enantiomeric purity, 100 μL of the solution was withdrawn by syringe and quenched into a solution of 5 mg of p-N,N-dimethylaminopyridine in 100 μL of triethylamine. (−)-α-Methoxy-α-(trifluoromethyl)phenylacetyl chloride (20 μL) or acetic anhydride (50 μL) was then added, and the mixture was shaken for 1 min. Chromatography (70×5 mm silica, petroleum either at first, then petroleum ether/ethyl ether (9/1) to elute) provided material of sufficient purity for NMR analysis. Analysis was accomplished using 250 MHz $^1$H NMR (C6D6). For the analysis of acetates, the shift reagent Eu(hfc)$_3$ was employed.

(b) Alternatively, for analysis of reaction extent, quenching into a mixture of 25 μL of sat. aq. sodium sulfate and 100 μL of ethyl ether, diluting with 400 μL of ethyl ether, and filtration gave a solution which could be analyzed by capillary GC (22 m SE-30, 60°-140°, helium carrier).

(c) For purposes of isolation of the epoxy alcohol, the reaction was quenched by addition of ethyl ether and 10% sodium hydroxide saturated with brine as described below.

(d) For purposes of isolation of the epoxy ester, the reaction mixture was treated with 2-3 eq. of triethylamine, 0.02 eq. of p-N,N-dimethylaminopyridine, and 1-3 eq. of acylating reagent (e.g., acetic anhydride or tosyl chloride) and stirred at 0° or room temperature for 1 to 4 hr. Evaporation of solvent and chromatography or distillation provided the pure ester.

(e) For purposes of isolation of a nucleophilically epoxide opened product, the reaction was quenched with 1-2 equivalents of a reducing agent (phosphine, phosphite, sulfide, hydride, etc.) then treated with the nucleophile (1-2 eq.) and titanium isopropoxide (1.2 eq.) as described below in Examples 4 and 5.

(10) Phosphate buffer (3M, pH7) was prepared by dissolving 1.5 mol of disodium hydrogen phosphate and 1.5 mol of potassium dihydrogen phosphate in enough water to make 1 L of solution, then adding sodium hydroxide to bring the pH to 7.0.

Table 1 indicates the results, employing the above-described procedure.

TABLE 1

| alcohol | % Ti | % tart | tartrate | rxn time | % yield | % ee |
|---|---|---|---|---|---|---|
| trans-2-hexen-1-ol | 5 | 6 | Et | 40 min | >95[b] | 90 |
| trans-2-hexen-1-ol | 10 | 12 | Et | 40 min | >95[b] | 93 |
| trans-2-hexen-1-ol | 5 | 7.5 | Et | 2 hr | 80[c] | 92 |
| trans-2-decen-1-ol | 5 | 7.5 | Et | 2 hr | 96 | >95 |
| cis-2-decen-1-ol | 10 | 15 | Et | 30 hr | 90 | 86 |
| cis-2-butene-1,4-diol monobenzyl ether | 10 | 12 | Et | 3 days | >95 | 85 |
| geraniol | 5 | 6 | Et | 15 min | >95 | 86 |
| geraniol | 5 | 7.5 | Et | 2 hr[d] | >95 | 93 |
| 1-hydroxymethyl-cyclohexene | 5 | 7.5 | Et | 3 hr[d] | 77[c] | 92 |
| allyl alcohol | 5 | 6 | iPr | 5 hr[e] | 98[b] | 89 |

[a]All yields are for isolated material of >95% purity by 250 MHz nmr, except as noted.
[b]GC yield.
[c]Isolated yield; loss due to volatility.
[d]Reaction carried out at −40° after catalyst preparation at −20°.
[e]Reaction carried out at 0° after catalyst preparation at −5°.

Example 2

(2S,3S)-3-heptyloxiranemethanol

A flame-dried 100 mL round bottom 3-necked (RB3N) flask (note 1) filled with thermometer, stopcock, septum, and stirbar was purged with argon, charged with 4 A molecular sieves (300 mg; note 2) and 30 mL of dichloromethane (note 3), and cooled to −22° (30% ethylene glycol/water/dry ice). R,R-(+)-diethyl tartrate (97 mg; 47 mmol; note 4) and titanium(IV)isopropoxide (91 mg; 0.32 mmol; note 5) were added, and the mixture was stirred at −22±2° for 10 min. t-Butyl hydroperoxide (2.2 mL of a 5.8M dichloromethane solution; note 6) was added, and the mixture was stirred at −22±2° for 30 min. A solution of trans-2-decen-1-ol (1.00 g; 6.4 mmol; note 7) in dichloromethane, was then added. The mixture was stirred under argon at −22±2° until analysis (note 8) indicated >95% reaction (2.5 hr).

The reaction was quenched (note 9) with a 10% aqueous sodium hydroxide solution saturated with sodium chloride (0.75 mL), diluted with 15 mL of anhydrous ethyl ether, removed from the cold bath, and with vigorous stirring, allowed to warm to 10°. After filtration through diatomaceous earth, the clear filtrate was re-treated with 0.75 mL of 10% sodium hydroxide/brine solution, this time stirring at room temperature for 15 min. Neutralization with 0.5 mL of phosphate buffer (note 10), treatment with 1.5 g of diatomaceous earth and 1.5 g of anhydrous magnesium sulphate, filtration through diatomaceous earth, and evaporation of solvent gave a white powder (1.10 g, 100%, mp 43.5°–48.5°), which by 250 MHz $^1$H nmr was of >95% chemical and optical purity. Recrystallization from petroleum ether provided white needles, mp 49.5°–50.0°. $[\alpha]_D^{25}$ −36.5° (c 2.8, HCCl$_3$, >97% ee).

Example 3

Preparation of (2S)-glycidol

An oven-dried 500 mL round bottom flask fitted with septum and stirbar was charged with 3 A powdered molecular sieves (3.5 g) and dichloromethane (190 mL). Under a nitrogen atmosphere, R,R-(+)-diisopropyl tartrate (1.25 mL, 5.95 mmol) and allyl alcohol (6.8 mL, 0.1 mol) were added and the solution was cooled to −5°. Titanium(IV)isopropoxide (1.5 mL, 5.0 mmol) was added, and the mixture was stirred at −5±2° for 10–30 min. Commercial grade 80% cumene hydroperoxide (0.2 mol, dried over 3 A powdered sieves) was added slowly over a period of 30 min. The mixture was stirred under nitrogen at −3±2° until analysis by GPLC (carbowax capillary, 70°) indicated >95% reaction (5 h).

The reaction was quenched by adding citric acid (1 g) in ether (100 to 200 mL). The cooling bath was removed and the mixture was stirred for 20–30 min. After filtration through a pad of diatomaceous earth, the filtrate was concentrated and distilled at reduced pressure to give glycidol (0.065 mol 65%, containing a small amount of cumene).

Example 4

In-situ opening of glycidol by benzenethiol

The asymmetric epoxidation was performed in exactly the same way as described above using 0.55 mL of allyl alcohol (8 mmol). After 5–6 hr at −3±2°, the reaction mixture was cooled to −25±5° and trimethyl phosphite (1.4 mL, 12 mmol) was added slowly. After stirring at −25±5° for 30 min the mixture was treated with benzenethiol (1.0 mL, 9.7 mmol) and titanium(IV)isopropoxide (3.0 mL, 10 mmol). The mixture was slowly warmed to room temperature and stirred for 1 hr.

The mixture was diluted with ether (20 to 40 mL), and 10% aqueous sulfuric acid (25 to 50 mL) was added. The mixture was stirred vigorously until two clear phases formed (1 hr). Phase separation, extraction with ethyl acetate and chromatographic purification provided (S)-3-phenylthio-1,2-propanediol as a white solid (1.290 g, 88%, mp 79°–81°, 89% ee).

Example 5

In-situ opening of glycidol by 1-naphthol; synthesis of (S)-propranolol

The asymmetric epoxidation was performed in exactly the same way as described above using 6.8 mL of allyl alcohol (0.1 mol). After 6 hr at −3±2° the reaction mixture was cooled to −25±5° and trimethyl phosphite (16 mL, 0.135 mol) was added slowly. The mixture was warmed to room temperature, then poured into a solution prepared under nitrogen from 1-naphthol (14.5 g, 0.10 mol) and NaH (2.4 g, 0.10 mol) in 400 mL of t.-butanol. Titanium(IV)isopropoxide (36 mL, 0.12 mol) was added and the mixture was stirred overnight at room temperature under nitrogen.

The reaction mixture was filtered through a pad of diatomaceous earth. The filtrate was concentrated to 150 mL and treated with 200 mL of 10% aqueous sulfuric acid as described above. Phase separation, extraction, and concentration gave a crude oil, which was dissolved in 150 mL of ether and treated with 100 mL of 1N aqueous sodium hydroxide (45 min at room temperature). Phase separation, extraction, and concentration provided crude (S)-3-(1-naphthoxy)-1,2-propanediol, which was carried on by known methods (Iriuchijima and Kojima, *Agric. Biol. Chem.* (1982) 46: 1153) to give crude (S)-propranolol hydrochloride (21.63 g, 73.2% from allyl alcohol). Recrystallization from methanol-ether afforded 15.00 g of the product (50.8%). Further recrystallization from methanol-ether provided white crystals of enantiomerically pure (S)-propranolol hydrochloride (12.56 g, mp 192.5°–193.5°; $[\alpha]_D^{21}$ −25.7°, c 1.18, ethanol).

It is evident from the above results that the subject method provides a substantial improvement over the prior discovery as described in U.S. Pat. No. 4,471,130. By ensuring the substantial absence of water during the course of the reaction, so that any water formed in situ is rapidly removed, the rate of the reaction is enhanced, yields and enantiomeric efficiencies are improved, and greatly improved results are obtained with the small olefinic alcohols which give water soluble epoxy alcohols. Furthermore, the isolation procedures are greatly simplified due to the much smaller amounts of tartrate ester and titanium containing compounds which must be removed at the end of the reaction. Thus, by using inexpensive reagents, such as molecular sieves or their equivalent, great economies are achieved in the epoxidation of a wide variety of olefinic alcohols. In this manner, the utility of the patented epoxidation method is greatly expanded, so as to be applied to a wide variety of syntheses, which would not otherwise be economical.

Although the foregoing invention has been described in some detail by way of illustration and example for purposes of clarity of understanding, it will be obvious that certain changes and modifications may be practiced within the scope of the appended claims.

What is claimed is:

1. In a method employing a titanium chiral glycol alkoxide catalyst, an olefinic alcohol, where the olefin is separated from the carbinol carbon atom by from 0 to 1 carbon atom, and an organic hydroperoxide in an inert dry medium under mild conditions below about 30° C., whereby the olefin is asymmetrically epoxidized, the improvement which comprises:

epoxidizing the olefin in the presence of from about 1-25 mol percent based on olefin of said catalyst under conditions where any water formed is continuously removed from the reaction mixture by means of a dehydrating agent.

2. A method according to claim 1, wherein said catalyst is prepared in the presence of a dehydrating agent.

3. A method according to claim 2, wherein said dehydrating agent is activated molecular sieves.

4. A method according to claim 2, where tert.-butyl hydroperoxide is the hydroperoxide.

5. A method according to claim 2, wherein cumene hydroperoxide is the hydroperoxide.

6. A method according to claim 1, wherein said dehydrating agent is activated molecular sieves.

7. A method according to claim 2, including the additional step of combining in situ the product of said epoxidation with an acylating agent to produce the epoxy ester.

8. In a method for preparing glycidol from allyl alcohol, wherein a titanium chiral glycol alkoxide catalyst is combined with allyl alcohol and a hydroperoxide in an inert anhydrous halohydrocarbon medium under mild conditions at a temperature in the range of about $-100°$ to 20° C., whereby said allyl alcohol is epoxidized to glycidol, the improvement which comprises:

preparing said catalyst in the presence of activated molecular sieves; and including in said inert medium in an amount sufficient to adsorb any water which is formed, activated molecular sieves, wherein said catalyst is present in from about 1-25 mol percent based on olefin.

9. A method according to claim 8, wherein said hydroperoxide is cumene hydroperoxide.

* * * * *